US006380165B1

(12) United States Patent
Al-Abed et al.

(10) Patent No.: US 6,380,165 B1
(45) Date of Patent: *Apr. 30, 2002

(54) IMMUNOLOGICAL ADVANCED GLYCATION ENDPRODUCT CROSSLINK

(75) Inventors: Yousef Al-Abed, New York, NY (US); Richard J. Bucala, Cos Cob, CT (US)

(73) Assignee: The Picower Institute for Medical Research, Manhasset, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,655

(22) Filed: Sep. 19, 1997

(51) Int. Cl.$^7$ ............... A61K 38/00; A61K 31/535; A61K 31/415; A61K 38/16
(52) U.S. Cl. ............... 514/19; 514/235.8; 514/396; 514/398; 514/8
(58) Field of Search ............... 435/7.1; 424/235.8, 424/9.1, 9.2; 562/562; 514/396, 19, 17, 18, 235.8, 398; 568/305; 530/331, 345

(56) References Cited

U.S. PATENT DOCUMENTS

| 4,665,192 A | * | 5/1987 | Cerami et al. | 548/336 |
|---|---|---|---|---|
| 5,624,804 A | | 4/1997 | Bucala | 435/7.1 |
| 5,629,408 A | | 5/1997 | Bucala | 530/413 |
| 5,811,401 A | * | 9/1998 | Bucala et al. | 514/19 |

FOREIGN PATENT DOCUMENTS

| EP | 0 322 402 A | * | 6/1989 |

OTHER PUBLICATIONS

Al–Abed et al. Bioorg. Med. Chem. Lett. 5: 2929–2930, 1995.*
Vasan et al. Nature 383: 275–278, 1996.*
Westwood et al. J. Protein Chem. 14: 359–372, 1995.*
Bucala et al. Adv. Pharmacol. 23: 1–34 (cited as reference A), 1992.*
Al–Abed et al. In: Peptides: Chemistry, Structure and Biology. (Ed) Pravin et al. Mayflower Scientific Ltd., 1996.*
Al–Abed et al. A novel AGE crosslink that exhibits immunological crossreactivity with in vivo–formed AGEs. Diabetes 46: Suppl. 1: A071, 1997.*
Bucala et al. In: Advanced glycosylation endproducts in post–translational modification of proteins. (Ed) Harding JJ. Crabbe MJC, Boca Raton: CRC Press, 2: 53–79, 1992.*
Brownlee et al. J. Exp. Med. 158: 1739–1744, 1983.*
Munch et al. Eur. J. Clin. Chem. Clin. Biochem. 35: 669–677, Sep. 1997.*
Chou et al. Mol. Med. 4: 324–332, 1998.*
Makita et al. Lancet 343: 1519–1522, 1994.*
Araki et al. J. Biol. Chem. 267: 10211–10214, 1992.*
Makita et al. J. Biol. Chem. 267: 5133–5138, 1992.*
Kohn et al. Diabetes 33: 57–59, 1984.*
Al–Abed et al. Roy. Soc. Chem. 223: 239–244, 1998.*
Al–Abed et al. Chem. Res. Toxicol. 10: 875–879, 1997.*
Al–Abed et al. Biorg. Medic. Chem. Lett. 6: 1577–1578, 1996.*
Nakarama et al. Biochem. Biophys. Res. Commun. 162: 740–745, 1989.*
Horiuchi et al. J. Biol. Chem. 266: 7329–7332, 1991.*
Odani et al. Nippon IYO Masu Superkutoru Gakkai Koenshu 22: 103–106, 1997.*
Makita et al. Science 258: 651–653, 1992.*
Osawa et al. Main Group Met. Chem. 258: 651–653, 1992.*
Pischetsrieder et al. J. Agric. Food Chem. 45: 2070–2075, 1997.*
Beisswenger et al. Diabetes 44: 824–829, 1995.*
K Uchida et al. FEBS Lett. 410(2,3): 313–318, 1997.*
H Fumikata et al. Biosci. Biotechnol. Biochem. 60(11): 1820–1825, 1996.*
K Nakamura et al. Main Group Met. Chem. 19(5): 301–306, 1996.*
EJ Menzel et al. Ann. Clin. Biochem. 33(3): 241–248, 1996.*
KJ Wells–Knecht et al. Nephrol. Dial. Transplant. 11(Suppl) 5: 41–47, 1996.*
ME Westwood et al. J. Protein Chem. 14(5): 359–372, 1995.*

\* cited by examiner

*Primary Examiner*—S. Devi
(74) *Attorney, Agent, or Firm*—Piper Marbury Rudnick & Wolfe; Steven B. Kelber

(57) ABSTRACT

There is disclosed a means for standardizing a kit that provides a means for measuring the formation of advanced glycosylation endproducts (AGEs). The present invention further provides a novel isolate AGE that is antigenic and useful for forming antibodies having utility in diagnostic assays and for standardizing diagnostic assays.

3 Claims, 2 Drawing Sheets

IMMUNOLOGICAL ADVANCED GLYCATION ENDPRODUCT CROSSLINK

TECHNICAL FIELD OF THE INVENTION

The present invention provides an advanced glycation endproduct (AGE) crosslink that exhibits immunological crossreactivity with in vivo AGEs.

BACKGROUND OF THE INVENTION

The glycation reaction is manifest by the appearance of brown pigments during the cooking of food, identified by Maillard in 1912. Maillard observed that glucose or other reducing sugars react with amino-containing compounds, including amino acids and peptides, to form adducts that under go a series of dehydrations and rearrangements to form stable brown pigments. Heat-treated foods undergo non-enzymatic browning as a result of a reaction between glucose and a polypeptide chain. Thus, pigments responsible for the development of brown color that develops as a result of protein glycosylation possessed characteristic spectra and fluorescent properties.

Subsequent reactions (including various dehydrations, oxidations, eliminations, condensations, cleavages and other chemical changes) occur to produce a vast array of "early" and "late" glycation adducts. More advanced glycation adducts are sometimes described as a class of yellow-brown, fluorescent pigments with intra- and intermolecular crosslinking activity. Specific glycation entities are thought to occur at low abundance within a widely divergent pool of advanced glycation endproducts (or AGEs). Despite significant research activity, the molecular structures of only a few of the later glycation adducts and products have been determined. Moreover, the contribution of these identified, in vivo-formed advanced glycation structures to biological processes is poorly understood. Therefore, there is a need in the art to identify AGEs and determine their biological properties.

The process of advanced glycation leads from the reversible interaction of reducing sugars with amino groups to the formation of more complex, irreversibly-bound structures with varied spectral and covalent cross-linking properties. These later products, termed advanced glycation endproducts or AGEs, form in vivo by chemical principles first described for the Maillard reaction (Ledl and Schleicher, *Angew. Chem. Int. Ed. Engl.* 29:565, 1990; and Maillard, *C. R. Hebd. Seances Acad. Sci.* 154:66, 1912). The potential significance of Maillard-type reactions in living systems however, has been appreciated only over the last 15 years and the term advanced glycation has come to refer specifically with those aspects of Maillard chemistry that involve macromolecules and which occur under physiological conditions. It is evident that AGEs form in living tissues under a variety of circumstances, and that they play an important role in protein turnover, tissue remodeling, and the pathological sequelae of diabetes and aging (Bucala and Cerami, *Adv. Pharm.* 23:1, 1992).

The initial event in protein glycation is the reaction of a reducing sugar such as glucose with the N-terminus of a protein or the ε-amnino group of a lysine to form an aldimine, or Schiff base. The Schiff base can hydrolyze back to its reactants or undergo an Amadori rearrangement to form a more stable $N^\epsilon$-(1-deoxy-1-fructosyl) lysine (Amadori product, AP). The reaction pathway leading to reactive crosslinking moieties (i.e. AGE formation) commences by further rearrangement or degradation of the AP. Possible routes leading from AP precursors to glucose-derived, protein crosslinks has been suggested only by model studies examining the fate of the AP in vitro. One pathway proceeds by loss of the 4-hydroxyl group of the AP by dehydration to give a 1,4-dideoxy-1-alkylamino-2,3-hexodiulose (AP-dione). An AP-dione with the structure of an amino-1,4-dideoxyosone has been isolated by trapping model APs with aminoguanidine, an inhibitor of the AGE formation (Chen and Cerami, *J Carbohydrate Chem.* 12:731, 1993). Subsequent elimination of 5-hydroxy then gives a 1,4,5-trideoxy-1-alkylamino-2,3-hexulos-4-ene (AP-ene-dione), which has been isolated as a triacetyl derivative of its 1,2-enol form (Estendorfer et al., *Angew. Chem. Ent. Ed. Engl.* 29:536, 1990). Both AP-diones and AP-ene-diones would be expected to be highly reactive toward protein crosslinking reactions, for example, by serving as targets for the addition of a guanidine moiety from arginine or an ε-amino group from lysine.

Dicarbonyl containing compounds, such as methylglyoxal, glyoxal and deoxyglucosones, participate in condensation reactions with the side chains of arginine and lysine. For example, the addition of methylglyoxal to the guanidine moiety of arginine leads to the formation of imidazol-4-one adducts (Lo et al., *J. Biol. Chem.* 269:32299, 1994) and pyrimidinium adducts (Al-Abed et al., *Bioorg. Med. Chem. Lett.* 6:1577, 1996). In one study, Sell and Monnier isolated pentosidine, an AGE fluorescent crosslink which is a condensation product of lysine, arginine, and a reducing sugar precursor (Sell and Monnier, *J. Biol. Chem.* 264:21597, 1989) from human dura collagen. The mechanism of pentosidine formation remains uncertain but crosslinking requires that the lysine-bound, glucose-derived intermediate contain a dicarbonyl functionality that can react irreversibly with the guanidinium group of arginine.

Several lines of evidence have established that AGEs exist in living tissue (Bucala and Cerami, *Adv. Pharm.* 23:1, 1992), yet the identity of the major AGE crosslink(s) that forms in vivo remains uncertain. Recent phannacologically-based data nevertheless have affirmed the importance of the AP-dione pathway in stable crosslink formation (Vasan et al., *Nature* 3 82:275, 1996). The lack of precise data concerning the structure of AGEs has been attributed to the lability of AGE crosslinks to the standard hydrolysis methods employed to remove the protein backbone, and to the possible structural heterogeneity of the crosslinks themselves. Moreover, there is data to suggest that the pathologically-relevant crosslinks may not themselves be fluorescent (Dyer et al. *J. Clin. Invest.* 91:2463, 1993), a property that has been historically associated with AGE formation and almost universally used as an indicator of the Maillard reaction in vivo.

Hyperimmunization techniques directed against an AGE-crosslinked antigen produced both polyclonal and monoclonal antibodies that recognize in vivo formed AGEs (Makita et al., *J. Biol. Chem.* 267:1997, 1992). These antibodies made possible the development of immunohistochemical and ELISA-based technologies that were free of specificity and other technical problems associated with prior fluorescence-based assays, and provided the first sensitive and quantitative assessment of advanced glycation in living systems. These anti-AGE antibodies were found to recognize a class of AGEs that was prevalent in vivo but immunochemically distinct from previously characterized structures such as FFI, pentosidine, pyrraline, CML, or AFGP (Makita et al., *J. Biol. Chem.* 267:1992, 1992). The specific AGE epitope recognized by these antibodies increased as a consequence of diabetes or protein age on various proteins such as collagen, hemoglobin, and LDL (Makita et al., *J. Biol. Chem.* 267:1997, 1992; Makita et al., *Science* 258:651, 1992; Wolffenbuttel et al., *The Lancet* 347, 513, 1996; and Bucala et al. *Proc. Natl. Acad. Sci. U.S.A.* 91:9441, 1994). One particular polyclonal antibody species, designated "RU", has been employed in an ELISA assay tested in human clinical trials. Immunoreactive AGEs were found to be inhibited from forming by administration of the pharmacological inhibitor, aminoguanidine (Makita et al., *Science* 258:651, 1992; and Bucala et al. *Proc. Natl. Acad. Sci. U.S.A.* 91:9441, 1994), and to provide important prognostic information correlated to diabetic renal disease (Beisswenger et al. *Diabetes* 44:824, 1995).

Despite the increasing body of data implicating the advanced glycation pathway in the etiology of such age- and diabetes-related conditions as atherosclerosis, renal insufficiency, and amyloid deposition, elucidation of the structure(s) of the pathologically important, AGE-crosslinks that form in vivo has been a challenging problem. Investigations of AGEs that form in vivo have necessarily relied on chemical methods to purify the crosslinking moieties away from their macromolecular backbones. These studies have led to a recognition that the major crosslinks which form in vivo are largely acid-labile and non-fluorescent (Bucala and Cerami, *Adv. Pharm.*, 23:1, 1992; Sell and Monnier, *J. Biol. Chem.* 264:21597, 1989; and Dyer et al. *J. Clin. Invest.* 91:2463, 1993). However, in view of a predictive antibody-based (ELISA) diagnostic assay, there is a need in the art to isolate and identify immunogenic AGEs that can be used to both standardize and improve such diagnostic assays. The present invention was made in an effort to achieve the foregoing goals. Further, there is a need in the art to measure formation of advanced glycosylation endproducts in all applications where protein aging is a serious detriment. This includes, for example, the area of food technology (ie., determination of the amount of food spoilage), perishability or shelf-life determination of proteins and other amino-containing biomolecules.

SUMMARY OF THE INVENTION

The present invention provides a means for standardizing a kit that provides a means for measuring the formation of AGEs as a diagnostic assay. The present invention further provides a novel isolate AGE that is antigenic and useful for forming antibodies having utility in diagnostic assays and for standardizing diagnostic assays.

The invention provides a condensation product advanced glycation endproduct (AGE) comprising a lysine component, an arginine component and a reducing sugar component. Preferably, the condensation product is an AGE according to formula I:

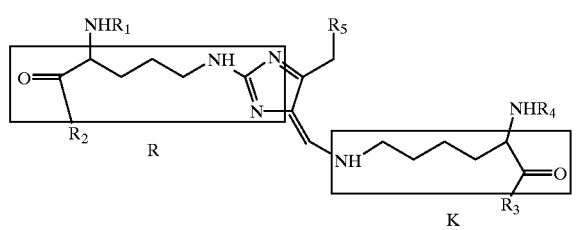

I wherein the lysine component is indicated by the box labeled "K"; the arginine component is indicated by the box labeled "R"; and the reducing sugar component is not boxed; and wherein $R_1$ and $R_4$ are independently H or an amide bond to an amino acid residue or a peptide chain; $R_2$ and $R_3$ are, independently, OH or an amide bond to an amino acid residue or a peptide chain; $R_5$ is H, $CH_2OH$ or $CHOHCH_2OH$; and wherein if more than one of $R_1$, $R_2$, $R_3$ or $R_4$ is an amide bond, then the lysine "K" component and the arginine "R" component may be amino acid residues of the same or a different peptide chain. Most preferably, the condensation product is an ALI having the structure:

II

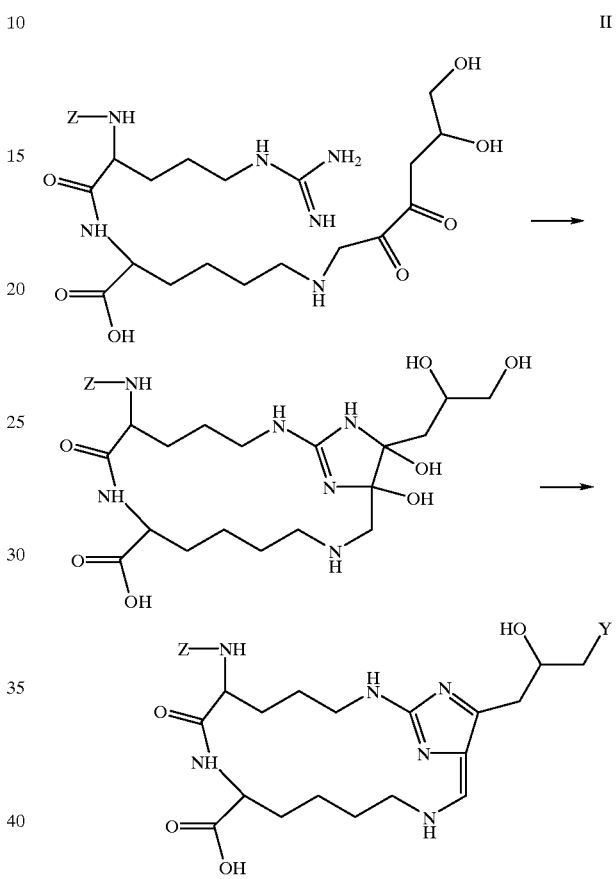

wherein Z is H, carboxybenzoyl, or the remainder of the polypeptide linked to the Arg and Lys groups; and Y is OH or the remainder of the polypeptide.

The present invention further provides a method for increasing macrophage recognition and elimination of advanced glycosylation endproducts, comprising administering to a mammal a therapeutic amount of a compound of formula I.

DETAILED DESCRIPTION OF THE INVENTION

Figure 1:
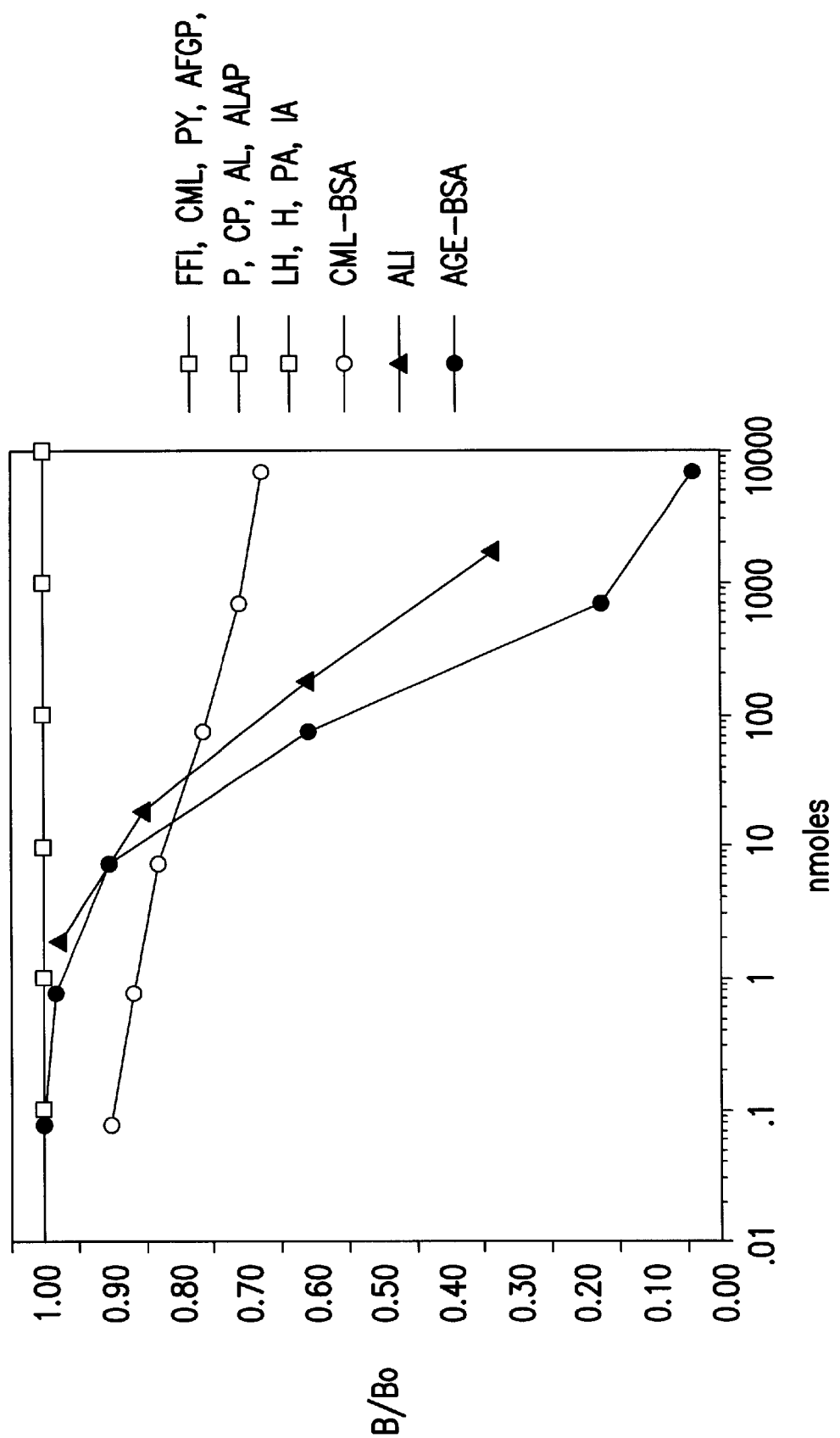
FIG. 1 shows the dose-dependent activity of synthetic ALI in an anti-AGE antibody-based competitive ELISA to measure AGE content. The binding curve is steep and shows 50% inhibition at 500 nmoles. For comparison purposes, the reactivity of FFI, CML, AFGP, pentosidine and cyclic pentosidine, and ligands with related epitope structure, such as $N^\alpha$-Z-arg-lys, $N^\alpha$-Z-arg-lys-AP, an imidazolium adduct, a pyrimidinium adduct, histidine, and lys-his, were studied. ELISA competition curves for the polyclonal anti-AGE antibody "RU" followed the methods described by Makita et al. (*J. Biol. Chem.* 267:1992, 1992). Assays employed glucose-derived, AGE-BSA as the absorbed antigen. FFI: 4-furanyl-2-furoyl-1H-imidazole (Ponger et al,. *Proc. Natl. Acad Sci. U.S.A.* 81:2684, 1984), CML: carboxymethyllysine (Ahmed et al., *J. Biol. Chem.* 261:4889, 1986), AFGP: 1-alkyl-2-formyl-3,4-diglycosylpyrrole (Farmar et al., *J. Org. Chem.* 53:2346, 1988), PY: pyrraline (Njoroge et al., *Carbohydrate Res.* 167:211, 1987), P: pentosidine (Sell and Monnier, *J. Biol. Chem.* 264:21597, 1989), CP: cyclic pentosidine (CP) (Al-Abed et al., *Bioorg. Med. Chem. Lett.* 5:2929, 1995), AL: $N^\alpha$-Z-arg-lys (AL), ALAP: $N^\alpha$-Z-arg-lys-AP, H: histidine, LH: lys-his, PA: pyrimidinium adduct (Al-Abed et al., *Bioorg. Med. Chem. Lett.* 6:1577, 1996), and IA: imldazolium adduct (Brinkmann et al., *J. Chem. Soc. Perkin Trans.* I:2817, 1995) showed no detectable crossreactivity with the RU anti-AGE antibody. With the exception of ALI, none of these compounds showed detectable crossreactivity with anti-AGE antibodies shown previously to react with in vivo-formed AGEs.

The present invention was made by exploiting the specificity of anti-AGE antibodies reactive with in vivo-formed AGEs to identify novel crosslinking moieties contained within a synthetic mixture of AGEs. This selection method found a single, immunoreactive AGE that formed in 0.6% yield in a synthetic mixture consisting of glucose and a $N^\alpha$-blocked dipeptide, $N^\alpha$-Z-arg-lys, as reactants. ALI was highly reactive with the anti-AGE antibody "RU" and showed a steep binding curve at nmole amounts.

The present invention found a novel ALI AGE based upon intramolecular crosslinking of adjacent residues for the formation of pentosidine-type AGEs, using a lys-arg-type dipeptide. In particular, the present invention provides a means for standardizing a kit that provides a means for measuring the formation of AGEs as a diagnostic assay. The present invention further provides a novel isolate AGE that is antigenic and useful for forming antibodies having utility in diagnostic assays and for standardizing diagnostic assays.

The invention provides a condensation product advanced glycation endproduct (AGE) comprising a lysine component, an arginine component and a reducing sugar component, Preferably, the condensation product is an AGE according to formula I:

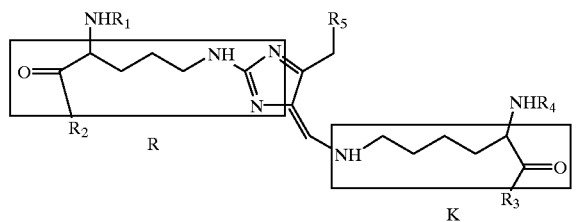

wherein the lysine component is indicated by the box labeled "K"; the arginine component is indicated by the box labeled "R"; and the reducing sugar component is not boxed; and wherein $R_1$ and $R_4$ are independently H or an amide bond to an amino acid residue or a peptide chain; $R_2$ and $R_3$ are, independently, OH or an amide bond to an amino acid residue or a peptide chain; $R_5$ is H, $CH_2OH$ or $CHOHCH_2OH$; and wherein if more than one of $R_1$, $R_2$, $R_3$ or $R_4$ is an amide bond, then the lysine "K" component and the arginine "R" component may be amino acid residues of the same or a different peptide chain. Most preferably, the condensation product is an ALI having the structure:

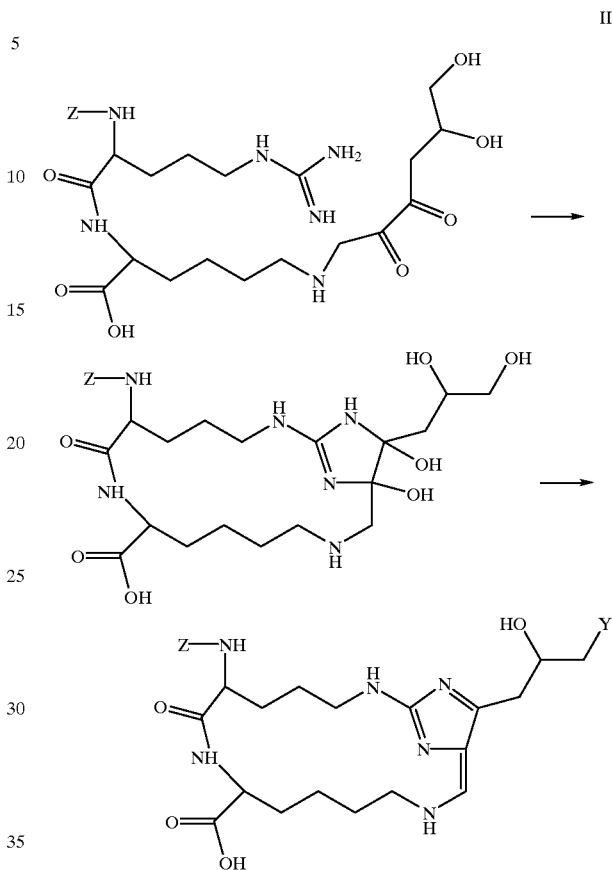

wherein Z is H, carboxybenzoyl, or the remainder of the polypeptide linked to the Arg and Lys groups; and Y is OH or the remainder of the polypeptide. The compounds of formula I were prepared by incubating one or more polypeptide containing arg and lys with a reducing sugar, such as ribose, glucose, fructose, ascorbate or dehydroascorbate, at physiological pH for periods of 10–300 hours and optionally at elevated temperatures for shorter periods of time. A preferred compound, such as ALI, is prepared by incubating a $N^\alpha$-blocked dipeptide (e.g., $N^\alpha$-Z-arg-lys) containing peptide (e.g., $N^\alpha$-CBZ-arg-lys) with a reducing sugar, such as ribose, glucose, fructose, ascorbate or dehydroascorbate, at physiological pH for periods of 10–300 hours and optionally at elevated temperatures for shorter periods of time. A preferred amine-protecting group is CBZ (carboxybenzyl) group due to its ease of removal and retention of stereochemistry during manipulations. The formed AGEs are purified, for example, by HPLC to provide the AGEs of formula I or formula II.

Among the biological activities of AGEs, the formation of stable crosslinks may be considered their most important pathological manifestation. The imidazole-based AGE of formula I, is a major species of the pathologically-important AGE crosslinks that form in vivo. The mechanism of formation of ALI points to the importance of the AP-dione as a critical, reactive intermediate and further affirms prior, pharmacologically-based studies that have implicated this intermediate, as well as its dehydration product, the AP-enedione in irreversible, protein-protein crosslinking (Vasan et al., *Nature* 382:275, 1996). These intermediates also have been implicated in the formation of the cyclization product cypentodine (Zhang and Ulrich, *Tetrahedron Lett.* 37:4667, 1996), which may display sufficient redox potential to participate in the oxidative reactions associated with phospholipid advanced glycation (Bucala et al., *Proc. Natl. Acad. Sci. U.S.A.* 90:6434, 1993; and Bucala, *Redox Reports* 2, 291, 1996).

Figure 2:
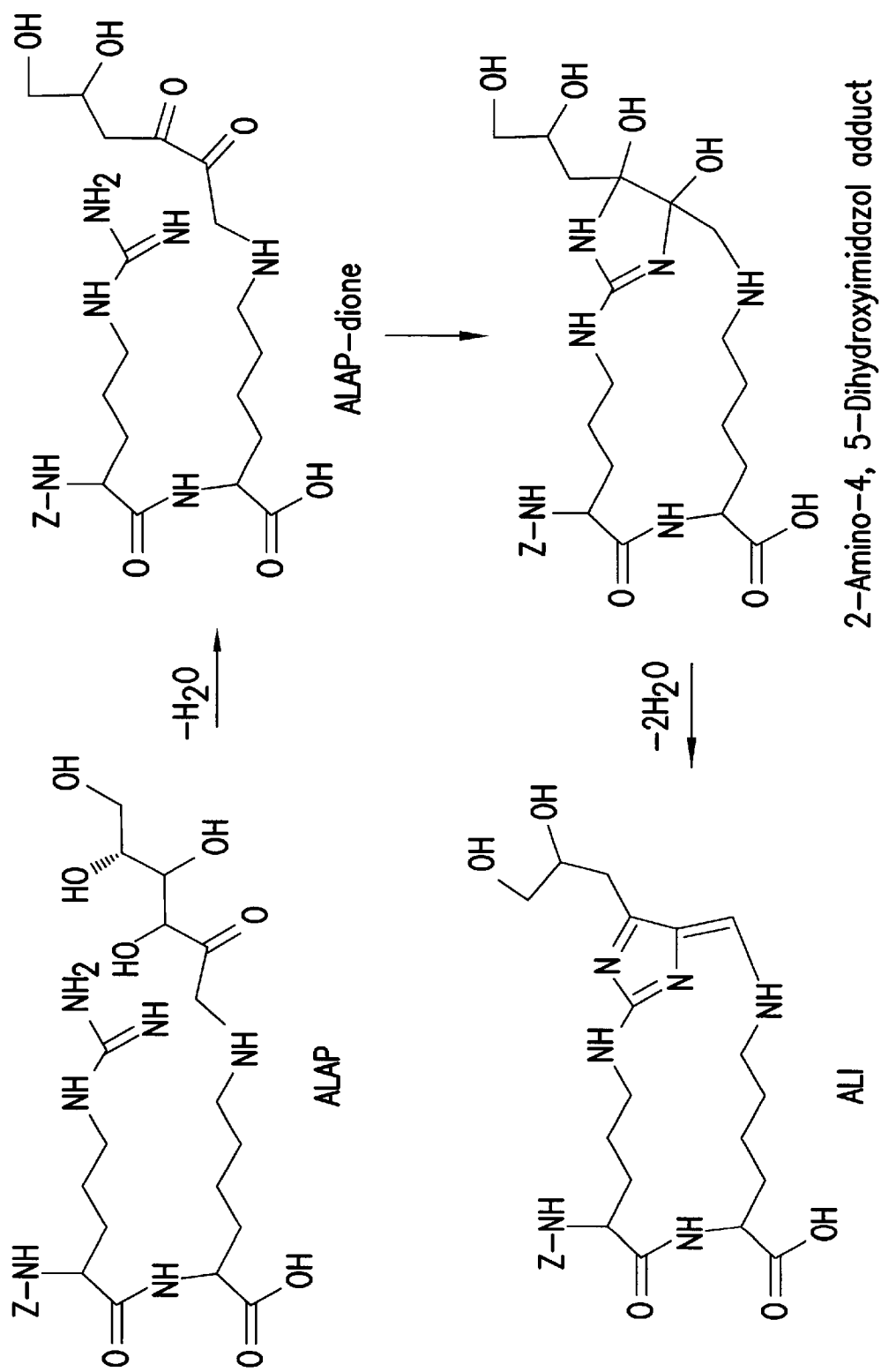
FIG. 2 shows a schematic to form the novel 2-amino-4,5 dihydroxyimidazol adduct as an intermediate and then the ALI AGE product through a dehydration reaction.

There are several possible in vivo synthetic routes leading from Amadori product precursors to glucose-derived protein crosslinks. Applicants have examined models examining the fate of the Amadori products in vitro. For instance, the Amadori product can undergo dehydration to give 1,4-dideoxy-1-alkylamino-2,3-hexodiulose (AP-dione) (FIG. 2). The dipeptide $N^\alpha$-Z-arg-lys was used as the AGE target. The proximity of arginine and lysine residues to each other promoted stable intramolecular crosslink formation. A $N^\alpha$-Z-arg-lys dipeptide was incubated with 10 equivalents of glucose in 0.2 M phosphate buffer (pH 7.4) at 37° C. for five weeks. This reaction mixture produced at least 25 distinct reaction products after fractionation of this mixture by HPLC. Each fraction was isolated, concentrated, and analyzed for its reactivity with a polyclonal anti-AGE antibody (RU) that has been shown previously to recognize a class of AGEs that increase in vivo as a consequence of hyperglycemia, and which are inhibited from forming in human subjects by treatment with the advanced glycation inhibitor aminoguanidine. The products present within one fraction (1.5% yield) were found to block antibody binding in a competitive ELISA assay for AGEs in a dose-dependent fashion. Therefore, the compound of formula I is useful to standardize AGE-based diagnostic assays as either a standard target or a standard competitor, or both. Further purification of this fraction by HPLC revealed the presence of one major (0.6% yield) immunoreactive compound. Characterization of this adduct by UV, ESMS and $^1$H-NMR spectra revealed the presence of an intramolecular arg-lys-imidazole crosslink (formula II). This crosslink is non-fluorescent and acid labile and may represent an important class of immunoreactive AGE-crosslinks that form in vivo.

EXAMPLE 1

This example illustrates a synthesis to prepare Arg-Lys-Imidazole (ALI). To a solution of $N^\alpha$-Z-arg-lys (1 g, 0.013 mmol) in 10 ml of aqueous 0.2 M phosphate buffer (pH 7.4) was added D-glucose (0.13 mmol). The reaction mixture was stirred at 37° C. for five weeks. At intervals, 10 µl of the reaction mixture was analyzed by HPLC using an analytical Primesphere column (5C18 MC, 5 micron, 250×4.6 mm, Phenomenex, Torrance, Calif.) and a binary solvent gradient consisting of 0.05% TFA in $H_2O$ (solvent A), and methanol (solvent B). Solvent was delivered at a flow rate of 1 ml/min as follows. From 0–30 min: a linear gradient from A:B (95:5) to A:B (25:75); from 30–45 min: a linear gradient from A:B (25:75) to (0:100). Detection was by monitoring UV absorption at λ 214, 254, 280, 320, and 350 nm. At least 25 distinct reaction products were identified upon fractionation of this mixture by HPLC. Larger amounts of these products were fractionated using a similar HPLC method (Primesphere column 5C18 MC, 5 micron, 250×21.2 mm, Phenomenex, Torrance, Calif.). Solvent was delivered at a flow rate of 10 mL/min using the same gradient as described above. The AGE crosslink eluted as a mixture of three components at 34.0 min. Further purification of this subfraction using the same method gave the desired compound in a high purity (>95%).

EXAMPLE 2

This example illustrates the discovery and isolation of the AGE of formula I. The dipeptide $N^\alpha$-Z-arg-lys was selected as a target, because a close association of the arginine and lysine residues provides a significant proximity effect that promotes crosslink formation. Moreover, a synthetic strategy employing an arg-lys dipeptide was used successfully in the past to isolate a cyclic pentosidine in a high yield (Beisswenger et al., *Diabetes* 44:824, 1995). $N^\alpha$-Z-arg-lys (13 mmoles) was incubated together with 10 equivalents of glucose in 0.2 M phosphate buffer (pH 7.4) for five weeks at 37° C. At least 25 distinct reaction products were identified upon fractionation of this mixture by reverse-phase HPLC. Each fraction was isolated, concentrated, and analyzed for its reactivity with anti-AGE antibody by ELISA (Makita et al., *J. Biol Chem.* 267:1992, 1992). Briefly, HPLC fractions and purified compounds were analyzed by an AGE-specific ELISA following methods described previously (Makita et al., *J. Biol. Chem.* 267:1992, 1992). This ELISA employed a polyclonal anti-AGE antibody raised by hyperimmunization against a heavily AGE-crosslinked preparation of ribonuclease. Total IgG was prepared by protein-G affinity chromatography and the ribonuclease backbone specificities removed by immunoabsorption. For assaying AGE immunoreactivity, 96-well round bottom microtitre plates (EIA/RIA plate, Costar, Cambridge, Mass.) first were coated with AGE-BSA (3 mg/ml, dissolved in 0.1 M sodium bicarbonate, pH 9.6) by incubation overnight at 4° C. After washing, the unbound sites were blocked with SuperBlock™ following the manufacturer's recommendations (Pierce, Rockford, Ill.). After washing, dilutions of test antigen, together with anti-AGE IgG, were added and the plates incubated at room temperature for 1 hr. The plates then were washed again and incubated with a secondary antibody (alkaline phosphatase-conjugated anti-rabbit IgG) at 37° C. for 1 hr. The unbound antibodies were removed by extensive washing and bound antibodies were detected by incubation with-nitrophenyl phosphate (pNPP) substrate for 30–60 min, and recording the optical density at 405 nm by an ELISA reader (EL309, Bio-Tek Instruments Inc., Burlington, Vt.). Results were expressed as $B/B_0$, calculated as [experimental OD—background OD (i.e. no antibody)]/ [total OD (i.e. no competitor)—background OD].

The product(s) contained within one distinct fraction, present in 1.5% yield, were found to block antibody binding in a dose-dependent fashion. Further purification of this fraction by HPLC revealed the presence of one major, immunoreactive compound (0.6% yield), together with two minor ones. The UV and fluorescence spectrum of the isolated, major product was unremarkable and similar to that of the starting material. The ESMS spectrum displayed a molecular ion of m/z 545 $[MH]^+$, an increase of 108 daltons compared to the starting material, $N^\alpha$-Z-arg-lys (MW: 436). A $^1$H-NMR spectrum in $D_2O$ showed, in addition to the $N^\alpha$-Z-arg-lys protons, five aliphatic protons that resonate as a multiplet between 2.35–4.65 ppm (5H), and an olefinic proton that resonates at 7.3 ppm within the Z-group. Overall, these data are consistent with the structure of a cyclic, arg-lys imidazole crosslink (ALI, formula II, FIG. 2).

EXAMPLE 3

This example illustrates a proposed mechanism of the AGE formation (FIG. 2). First, dehydration of the lysine-derived AP (which has been determined to form in 18% yield under these reaction conditions) gives an obligate, AP-dione reactive intermediate. Reversible addition of the guanidine moiety to the dicarbonyl yields the 2-amino-4,5-dihydroxyimidazole adduct, which then undergoes dehydration to deliver the stable cyclic ALI. Of importance, this crosslink is non-fluorescent, acid-labile, and can be inhibited from forming by aminoguanidine.

We claim:

1. An isolated advanced glycation endproduct (AGE) comprising a condensation product of a lysyl component, an arginyl component and a reducing sugar component, wherein the arginyl component and the reducing sugar component form a monocyclic substituted imidazole.

2. An isolated compound according to formula I:

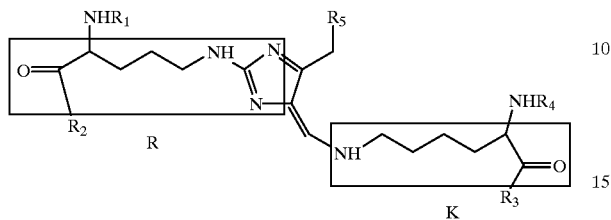

wherein a lysyl component is indicated by the box labeled "K"; an arginyl component is indicated by the boxy labeled "R"; and a reducing sugar component is not boxed; and wherein $R_1$ and $R_4$ are independently H or an amide bond to an amino acid residue or a peptide chain; $R_2$ and $R_3$ are, independently, OH or an amide bond to an amino acid residue or a peptide chain; $R_5$ is H, $CH_2OH$ or $CHOHCH_2OH$; and wherein if more than one of $R_1$, $R_2$, $R_3$ or $R_4$ is an amide bond, then the lysyl "K" component and the arginyl "R" component may be amino acid residues of the same or a different peptide chain.

3. An isolated compound having the structure:

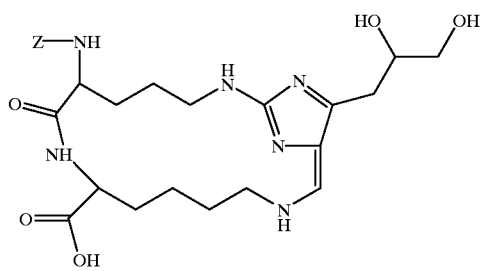

wherein Z is carboxybenzoyl, or H.

* * * * *